United States Patent [19]

Mueller et al.

[11] 4,177,056

[45] Dec. 4, 1979

[54] WATER-INSOLUBLE HYDROPHILIC COPOLYMERS USED AS CARRIERS FOR MEDICAMENTS AND PESTICIDES

[75] Inventors: Karl F. Mueller, New York; William R. Good, Yorktown Heights, both of N.Y.

[73] Assignee: Ciba-Geigy Corporation, Ardsley, N.Y.

[21] Appl. No.: 872,191

[22] Filed: Jan. 25, 1978

Related U.S. Application Data

[60] Division of Ser. No. 581,065, May 27, 1975, abandoned, which is a continuation-in-part of Ser. No. 483,743, Jun. 27, 1974, abandoned.

[51] Int. Cl.$^2$ ............................ A01N 9/22; A61K 31/78
[52] U.S. Cl. .................................... 71/93; 71/DIG. 1; 424/78; 424/81
[58] Field of Search ......... 424/81, 78; 71/93, DIG. 1; 260/859 R

[56] References Cited

U.S. PATENT DOCUMENTS

| | | | |
|---|---|---|---|
| 3,503,942 | 3/1970 | Seiderman | 526/320 |
| 3,509,234 | 4/1970 | Burrant | 260/859 R |
| 3,677,920 | 7/1972 | Kai | 260/859 R |
| 3,829,531 | 8/1974 | Graff | 260/859 R |
| 3,876,761 | 4/1975 | Shepherd | 424/78 |
| 3,959,237 | 5/1976 | Buank | 526/16 |
| 3,996,308 | 12/1976 | Douek | 260/859 R |
| 4,007,258 | 2/1977 | Cohen et al. | 424/22 |
| 4,056,496 | 11/1977 | Mancini et al. | 260/29.6 TA |

*Primary Examiner*—Leonard Schenkman
*Attorney, Agent, or Firm*—Luther A. R. Hall

[57] ABSTRACT

A water-insoluble hydrophilic gel comprising: (A) about 30 to about 90% of a hydrophilic (a) polymer of identical or different water-soluble mono-olefinic monomers, or (b) copolymer of said water-soluble monomers with 1 to 70% of water-insoluble, identical or different mono-olefinic monomers, which polymer or copolymer is cross-linked with (B) about 10 to about 70% of a terminal diolefinic hydrophobic macromer having a molecular weight from about 400 to about 8000.

20 Claims, No Drawings

WATER-INSOLUBLE HYDROPHILIC COPOLYMERS USED AS CARRIERS FOR MEDICAMENTS AND PESTICIDES

CROSS-REFERENCE TO RELATED APPLICATION

This is a Divisional of application Ser. No. 581,065, filed on May 27, 1975, now abandoned; which in turn is a continuation-in-part of application, Ser. No. 483,743, filed on June 27, 1974, now abandoned.

BACKGROUND OF THE INVENTION

This invention relates to cross-linked hydrophilic polymers which are suitable for use as a carrier for medicaments and other active ingredients; as hydrophilic membranes for separation processes; bandages for wound treatment; body implants, e.g. artificial veins and coatings on glass, metal, wood or ceramics, and in particular, for use in applications where strength of the polymer article and high permeability to water are required simultaneously.

It is known to produce sparingly cross-linked, water-insoluble but hydrophilic polymers which can be used as carriers for biologically active, at least slightly water-soluble substances by copolymerization of a major amount of hydrophiic mono-olefinic monomers and a minor amount ranging between 0.01 and 15% of said mono-olefinic monomers, of a low molecular weight cross-linker. As mono-olefinic monomers, particularly monoesters of acrylic or methacrylic acid with poly-functional alcohols, such as ethyleneglycol monomethacrylate, and as cross-linking agents particularly diesters of said acids with said alcohols, such as ethyleneglycol bis-methacrylate are used and the copolymerization is carried out in the presence of water, see U.S. Pat. No. 3,220,960 or a water-free system, see U.S. Pat. No. 3,520,949. Low molecular as well as macromolecular, water-soluble substances, such as polyethyleneoxide mono-methacrylate together with a minor amount of the corresponding bis-methacrylate have been used, U.S. Pat. No. 3,220,960, as monomers and cross-linking agents. The water-insoluble, but hydrophilic copolymers and the process for their production have been modified in several directions and adapted to specific purposes, e.g. the production of soft contact lenses, U.S. Pat. No. 3,220,960 and Reissue No. 27,401, and the copolymerization in the presence of linear polyamide resin in order to improve or modify the mechanical properties of shaped bodies formed from the obtained polymers, U.S. Pat. No. 3,520,949. However, in all modifications low molecular-weight poly-olefinic cross-linking agents, especially ethyleneglycol bis-methacrylate, were used in very small to moderate amounts never exceeding 20% of the amount of the mono-olefinic monomer. Though the copolymers of the type described above could be modified to comply with the requirements of several different modes of using them, the mechanical properties in either the unswollen, i.e. water-free, or the swollen, i.e. equilibrium state with water, could not be satisfactorily adapted to all modes of uses.

It is known that hydrophilic polymers whose major constituents are monoesters of acrylic acid and methacrylic acid and a bi-functional alcohol have glass transition temperatures or softening points between 55° C. and 80° C. For this reason said prior art articles are brittle and glassy in the dry state at temperatures below 55° C. After equilibration in water the articles of said prior art becomes soft and somewhat pliable but also weak with respect to their flexural properties. In addition, said prior art articles are very susceptible to tearing shear forces if they are knicked or injured in any way.

In order to avoid the undesirable weak characteristics of articles produced by said prior art, a medium made of a stronger polymeric material is used as physical support, or the pre-polymerized mixture is filled with an insoluble material such as silica gel. These techniques, although they afford a certain amount of cohesive strength (the hydrogel material acting as a glue), produce articles which are still susceptible to glassy fracture in the dry state and shear fracture in the swollen state within the interstitial regions of the article. By the same token, addition of fillers to the prepolymer modify the diffusion properties and water premeability of the articles.

SUMMARY AND OBJECTS OF THE INVENTION

It is an object of the present invention to provide cross-linked hydrophilic copolymers having high flexibility and high elasticity both in substantially water-free state and in the swollen state, i.e. in equilibrium with water or aqueous fluids, such as animal body fluids, which are suitable for use as hydrophilic membranes for separation processes, bandages for wound treatment; body implants, e.g. artificial veins, and coatings on glass, metal, wood or ceramics, and as a carrier for biologically active substances, e.g. drugs, herbicides, insecticides, fungicides, bactericides, and fragrances.

It is a further object of the invention to provide cross-linked hydrophilic copolymers suitable as described above, which possess a high tensile strength in the swollen state.

It is a still further object of the invention to provide cross-linked hydrophilic copolymers, which possess the above-named improved properties and contain a variable, effective amount of biologically active materials, in particular, therapeutically active substances.

It has now been found that water-insoluble hydrophilic copolymers consisting essentially of a hydrophilic polymer of mono-olefinic monomers cross-linked with a major amount of a diolefinic non-hydrophilic macromer and which may contain a biologically active substance, possess the above-named and further desirable properties. In the novel copolymers, the proportion of the terminal diolefinic non-hydrophilic macromer is higher than that of the cross-linking agents in the known hydrophilic copolymers and is a major proportion of the system amounting to about 10 to about 70% of the hydrophilic polymer or preferably from about 15 to about 50%. The said terminal diolefinic non-hydrophilic macromer has a molecular weight between about 400 and about 8000 or preferably between about 600 and 5000.

DESCRIPTION OF THE PREFERRED EMBODIMENTS

The present invention comprises an insoluble polymeric hydrogel which is suitable for use as a carrier for medicaments to be delivered to an organism orally, buccally or in the form of a subcutaneous or intramuscular implant. The hydrogels of this invention may also be fashioned into body implants, such as artificial veins, devices for insertion into the urethra, vagina, or anal cavity, or fashioned in bandage form for controlled delivery of the medicament through the skin. Other applications with the novel, water-swellable gels are membranes for reverse osmosis and semi-permeable membranes; as hydrophilic membranes for separation processes; bandages for wound treatment; coatings on glass, metal, wood or ceramics and, in short, applications where hydrophilicity and strength are both simultaneously required.

The novel hydrogels of this invention are synthesized by free radical copolymerization, either in solution or in bulk, of a water-soluble monomer, (As) capable of forming a water-soluble or water-swellable polymer, i.e. hydrophilic polymer (Ap), with a di-olefinic non-hydrophilic macromer (B), for example, a divinyl compound having a long, linear polycondensate chain, such as polytetramethylene ether, terminated on both ends with a polymerizable vinyl group. In this way a three-dimensional macromolecular network is formed composed of two types of segments, each segment contributing its distinct physical property to the system. The A-segment contributes water-solubility; the hydrophobic B-segment forms flexible cross-links. By varying the relative proportions of each compound, a wide range of mechanical and diffusional properties may be obtained. For example, polymers having excellent strength and elongation as well as toughness, and yet being capable of absorbing as much as approximately their own weight of water, can be obtained by using the proper relative proportions of A and B. This is in contrast to conventional hyrogels, whose cross-links are short and non-elastic and which, in the dry state, are hard and brittle.

The novelty of the polymers of the present invention is the incorporation of the di-functional macromolecule B as a major proportion of this system. In this manner, the di-functional macromer does not only serve as a structural cross-link, but also imparts its unique physical properties to the gel.

The hydrophilic polymer, Ap, is preferably a polymer of one or several water-soluble mono-olefinic monomers, As, but it may also be a copolymer of mono-olefinic water-soluble monomers, and at most 70%, preferably at most 50%, of the total amount of monomers, of a water-insoluble mono-olefinic monomer, Ai. The water-soluble monomers are preferably acrylic and/or methacrylic acid (2-methylacrylic acid) or water-soluble derivatives thereof, such as their hydroxyalkyl esters, e.g., 2-hydroxyethyl, 3-hydroxypropyl, 2-hydroxypropyl or 2,3-hydroxypropyl esters; also ethoxylated and polyethoxylated hydroxyalkyl esters, such as esters of alcohols of the formula

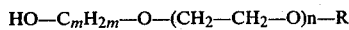

$$HO-C_mH_{2m}-O-(CH_2-CH_2-O)_n-R$$

wherein
R represents hydrogen or methyl,
m represents 2 to 5 and
n represents 1 to 20 or esters of analogous alcohols, wherein a part of the ethyleneoxide units is replaced by propyleneoxide units. Further suitable esters are dialkylaminoalkyl acrylates and methacrylates, such as the 2-(dimethylamino)-ethyl-, 2-(diethylamino)-ethyl- and 3-(dimethylamino)-2-hydroxypropyl esters. Another class of suitable derivatives of such acids are their water-soluble amides, such as the unsubstituted amides and amides substituted by lower hydroxyalkyl, lower oxaalkyl- or lower dialkylaminoalkyl groups such as N-(hydroxymethyl)-acrylamide and -methacrylamide, N-(3-hydroxypropyl)-acrylamide, N-(2-hydroxyethyl)-methacrylamide, N-(1,1-dimethyl-3-oxabutyl)-acrylamide and N-[1,1-dimethyl-2-(hydroxymethyl)-3-oxabutyl]-acrylamide; water-soluble hydrazine derivatives, such as trialkylamine methacrylimide, e.g., trimethylamine-methacrylimide and dimethyl-(2-hydroxypropyl)amine methacrylimide and the corresponding derivatives of acrylic acid; mono-olefinic sulfonic acids and their salts, such as sodium ethylene sulfonate, sodium styrene sulfonate and 2-acrylamido-2-methylpropanesulfonic acid; N-[2-(dimethylamino)-ethyl]-acrylamide and -methacrylamide, N-[3-(dimethylamino)-2-hydroxypropyl]-methacrylamide, or mono-olefinic derivatives of heterocyclic nitrogen-containing monomers, such as N-vinyl-pyrrole, N-vinyl-succinimide, 1-vinyl-2-pyrrolidone, 1-vinyl-imidazole, 1-vinyl-indole, 2-vinyl-imidazole, 4(5)-vinyl-imidazole, 2-vinyl-1-methyl-imidazole, 5-vinyl-pyrazoline, 3-methyl-5-isopropenyl-pyrazole, 5-methylene-hydantoin, 3-vinyl-2-oxazolidone, 3-methacrylyl-2-oxazolidone, 3-methacrylyl-5-me-2-oxazolidone, 3-vinyl-5-methyl-2-oxazolidone, 2- and 4-vinyl-pyridine, 5-vinyl-2-methyl-pyridine, 2-vinyl-pyridine-1-oxide, 3-isopropenyl-pyridine, 2- and 4-vinyl-piperidine, 2- and 4-vinyl-quinoline, 2, 4-dimethyl-6-vinyl-s-triazine, 4-acrylyl-morpholine.

These monomers can be used alone or in combination with each other and other suitable vinyl monomers, which may also be hydrophobic. The amount of such hydrophobic monomers shall not exceed 60 percent of the total composition and is preferably below 40 percent.

Suitable hydrophobic monomers are, for example, water-insoluble olefinic monomers, such as alkyl acrylates or methacrylates in which alkyl has 1 to 18 carbon atoms, e.g., methyl and ethyl methacrylate or acrylate; vinyl esters derived from alkanecarboxylic acids having 1 to 5 carbon atoms, e.g., vinyl acetate, acrylonitrile, styrene, and vinyl alkyl ethers in which the alkyl portion of the ether chain has 1 to 5 carbon atoms, e.g., (methyl, ethyl, propyl, butyl or amyl)-vinyl ether.

Water-soluble monomers which require a comonomer for polymerization are maleates, fumarates and vinylethers; the following monomer combinations are, for instance, useful: di-(hydroxyalkyl) maleates, such as di-(2-hydroxyethyl) maleate, and ethoxylated hydroxyalkyl maleates, hydroxyalkyl monomaleates, such as 2-hydroxyethyl monomaleate and hydroxylated hydroxyalkyl monomaleate with vinyl ethers, vinyl esters, styrene or generally any monomer which will easily copolymerize with maleates or fumarates; hydroxyalkyl vinyl ethers, such as 2-hydroxyethyl vinyl ether, 4-hydroxybutyl vinyl ether, with maleates, fumarates, or generally all monomers which will easily copolymerize with vinyl ethers.

Especially valuable as water-soluble monomers are hydroxyalkyl acrylates and methacrylates, such as: 2-hydroxyethyl acrylate, 2-hydroxyethyl methacrylate, 2-hydroxypropyl acrylate, 2-hydroxypropyl methacrylate, 2,3-dihydroxypropyl methacrylate, N-vinyl pyrrolidone, acrylic acid, methacrylic acid and a tert. amino-methacrylimide, e.g. trimethylamine-methacrylimide, as described in U.S. Pat. No. 3,527,802.

The most preferred monomers are 2-hydroxyethyl methacrylate and N-vinylpyrrolidone.

In the di-olefinic non-hydrophilic macromer, B, the olefinic moieties are preferably provided by acyl radicals of lower α, β-mono-unsaturated aliphatic monocarboxylic or dicarboxylic acids or by vinyloxy radicals. These radicals are linked by a macromolecular non-hydrophilic chain containing repeating ester, amide or urethane, but particularly ether linkages. The molecular weight of the chain may vary from about 400 to about 8000, preferably between about 600 and 5000 and, especially, between about 1500 an 3000. Thus, the constituent B preferably corresponds to the formulae

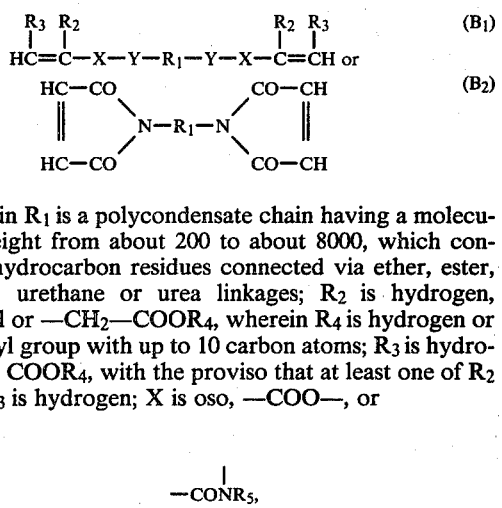

wherein $R_1$ is a polycondensate chain having a molecular weight from about 200 to about 8000, which contains hydrocarbon residues connected via ether, ester, amide, urethane or urea linkages; $R_2$ is hydrogen, methyl or $—CH_2—COOR_4$, wherein $R_4$ is hydrogen or an alkyl group with up to 10 carbon atoms; $R_3$ is hydrogen or $COOR_4$, with the proviso that at least one of $R_2$ and $R_3$ is hydrogen; X is oso, —COO—, or

wherein $R_5$ is hydrogen or alkyl with up to 5 carbon atoms and Y is a direct bond or the radical $—R_6—Z_1—CO—NH—R_7—NH—CO—Z_2—$, wherein $R_6$ is linked to X and represents branched or linear alkylene with up to 7 carbon atoms; $Z_1$ and $Z_2$ is oxo or $NR_5$, and $R_7$ is the diradical of aliphatic or aromatic diisocyanate, with the proviso that in case X is oxo, Y is different from a direct bond and $R_2$ and $R_3$ are hydrogen.

In the compounds of formula $B_1$ and $B_2$, $R_1$ is in particular a poly-propylene oxide chain or a poly-tetramethylene oxide chain, but it can also represent a chain derived from dicarboxylic acids, diols, diamines or diisocyanates etc., by well known methods of polycondensation. The terminal radicals of the compounds of formula $B_1$ are according to the definitions of $R_2$ and $R_3$ and if X represents —COO— or $—CONR_5$—, the acyl radicals of acrylic or methacrylic acid or the monoacyl radicals of maleic, fumaric or itaconic acid, or of monoalkyl esters of these acids with straight or branched chain alkanols of 1 to 10 carbon atoms, such as methanol, ethanol, butanol, diisobutyl alcohol or decanol, or if X represents oxygen, the vinyloxy radical of vinyl ethers. Compounds of the formula $B_1$ with Y being a direct bond are diesters of macromolecular diols, wherein two hydroxy groups are attached to the polycondensate chain $R_1$ in opposite terminal or almost terminal positions, with α,β-unsaturated acids. Such diester can be prepared from said macromolecular diol by well-known acylation methods using reactive functional derivatives of suitable acids, e.g. chlorides of acrylic or methacrylic acid, or of monoalkylesters of maleic, fumaric or itaconic acid, or the anhydride of maleic or itaconic acid. Compounds of formula $B_1$ with amide group X are diamides obtained from macromolecular diamines by well-known acylation reactions using e.g., the acid chlorides or anhydrides mentioned above. The macromolecular diamines are prepared e.g. by reacting corresponding macromolecular diols with twice the molar amount of an alkyleneimine e.g. propyleneimine.

The macromolecular bis-maleamic acids obtained by the above reaction when maleic acid anhydride is used as the acylating agent for macromulecular diamines can be further heated or reacted with dehydrating agents to yield the macromolecular bis-maleimido compounds of formula $B_2$. In these compounds, $R_1$ thus may be e.g. one of the macromolecular polycondensate chains named as moieties of compounds of the formula $B_1$.

According to the definition of formula $B_1$, Y can further be a divalent radical $—R_6—Z_1—CONH—R_7—NH—CO—Z_i—$. Therein $R_6$ is, e.g. methylene, propylene, trimethylene, tetramethylene, pentamethylene, neopentylene (2,2-dimethyltrimethylene), 2-hydroxytrimethylene, 1,1-dimethyl-2-(1-oxo-ethyl)-trimethylene or 1-(dimethylaminomethyl)-ethylene and in particular ethylene. The divalent radical $R_7$ is derived from an organic diisocyanate and is an aliphatic radical such as alkylene, e.g. ethylene, tetramethylene, hexamethylene, 2,2,4-trimethylhexamethylene, 2,4,4-trimethylhexamethylene; fumaroyldiethylene or 1-carboxypentamethylene; a cycloaliphatic radical, e.g. 1,4-cyclohexylene or 2-methyl-1,4-cyclohexylene; an aromatic radical, such as n-phenylene, p-phenylene, 2-methyl-m-phenylene, 1,2-, 1,3-, 1,5-, 1,6-, 1,7-, 1,8-, 2,3- and 2,7-naphthylene, 4-chloro-1,2- and 4-chloro-1,8-naphthylene, 1-methyl-2,4-, 1-methyl-2,7-, 4-methyl-1,2-, 6-methyl-1,3- and 7-methyl-1, 3-naphthylene, 1,8-dinitro-2,7-naphthylene, 4,4'-biphenylene, 3,3'-dichloro-4,4'-biphenylene, 3,3'-dimethoxy-4,4'-biphenylene, 2,2'-dimethyl- and 3,3'-dimethyl-4,4'-biphenylene, 2,2'-dichloro-5,5'-dimethoxy-4,4'-biphenylene, methylenedi-p-phenylene, methylenebis-(3-chlorophenylene), ethylenedi-p-phenylene or oxydi-p-phenylene. If in structure $B_1$, Y is no direct bond, $R_6$ is always connected to X.

Thus, compounds of the formula $B_1$, in which Y is said divalent radical, are, if X represents oxygen, bis-vinylethers or, if X represents —COO— or

bis-acrylates, bis-methacrylates, bis-maleates, bis-fumarates and bis-itaconates.

The more preferred divinyl macromers, B, consist of polytetramethylene oxide glycols of molecular weight of about 1000 to about 4000, endcapped with 2,4-toluene-diisocyanate and reacted with about 2 mols of 2-hydroxyalkyl acrylates or methacrylates. Especially valuable is that macromer consisting of polytetramethylene-oxide glycol of molecular weight of about 1500 to about 3000, endcapped with 2,4-toluene diisocyanate and reacted with about 2 moles of 2-hydroxyethyl methacrylate.

The novel hydrophilic copolymers of this invention are produced by free radical copolymerization, either in solution or in bulk, of water-soluble mono-olefinic monomers As or a mixture of at least 30% of water-soluble monomers As with at most 70% of water-insoluble mono-olefinic monomers Ai with from 10 to 70%, with reference to the total weight of the hydrogel, of macromers of the formula $B_1$ or $B_2$. The polymerization is suitably carried out with a free radical generating initiator at a temperature in the range from about 40° C. to about 150° C., the preferred temperature ranges between about 50° C. and about 100° C. If a therapeutically or otherwise biologically active substance is present during the polymerization, its heat stability may be a limiting factor on the polymerization temperature.

One preferred method of preparing the hydrogel article comprises dissolving into the macromer-monomer solution prior to polymerization, the desired concentration of the medicament along with macromer monomer ratio selected in such a way, as to produce the desired mechanical and water absorption characteristics for the hydrogel, incorporating from about 0.02% to about 1%, by weight, of a suitable free radical initiator and polymerizing the mixture at, e.g. 80° C. for about 2 hours in a closed mold so as to produce a flat sheet of hydrogel containing the medicament as a quasi-solid solution. The sheet is then subjected to a high vacuum at about 100° C. for about 12 hours in order to remove residual monomers and initiator decomposition products.

A preferred laboratory method for preparation of the hydrogel, in the form of a cylinder, comprises the filling of flexible polyethylene tubing with the preferred composition of macromer, monomers, medicament and catalyst and reacting the mixture for approximately 2 hours at 80° C. The finished article is removed by slitting the tubing longitudinally and stripping it away from the hydrogel article.

Yet another preferred method of preparation of the hydrogel, in the form of small spheres or beads, comprises the high speed stirring of the preferred composition of macromer, monomers, medicament and catalyst in a viscous medium which is not a solvent for any part of the hydrogel composition at about 90° C. Examples of suitable bead polymerization media are silicone oils, polyfluorinated oils and the like, e.g. mineral spirit and saturated aqueous salt solution.

Yet another preferred method of preparation of the hydrogel in the form of a foamed object comprises the admixing of a common blowing agent, such as sodium bicarbonate, into the preferred composition and polymerizing the mixture in a mold at about 80° C. for about 1 hour. The resulting closed cell foam is particularly suitable for fast water absorption and medicament delivery.

Compounds of the formula $B_1$, wherein Y is $-R_6-Z_1-CONHR_7-NH-CO-Z_2-$ are obtained in a 2-step reaction by first reacting macromolecular diols or diamines, i.e., compounds which contain two hydroxy or amino groups attached to the polycondensate chain, $R_1$, in opposite terminal or almost terminal positions, with at least twice the amount of an aliphatic, cycloaliphatic or aromatic diisocyanate consisting of two isocyanate groups attached to the radical $R_7$ and, second, reacting the macromolecular diisocyanates obtained with a compound of the formula

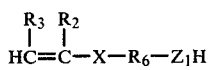  (C)

wherein $R_2$, $R_3$, X, $R_6$ and $Z_1$ have the meaning defined for ($B_1$) above.

If X represents oxygen, (C) is a vinylether containing an active hydrogen, for instance an hydroxy-alkyl vinylether or an aminoalkyl vinylether; if X represents —COO— or

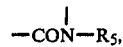

(C) is an acrylate, methacrylate, maleate, fumarate, itaconate or the corresponding amide, containing an active hydrogen in the alkyl group. The macromolecular diol or diamine is preferably used in a small excess, i.e., the ratio of isocyano groups to hydroxy or amino groups during the first step of the macromer synthesis should be at least 1:1, but is preferably at least 1:1.05 or lower. If the compound of formula C, used during the second step of the macromer synthesis, is the same as is used as the hydrophilic monomer $A_s$, then a' large excess of this compound can be used, so that the resulting solution of macromer $B_1$ dissolved or dispersed in monomer A can be used directly for the preparation of the final hydrophilic copolymer.

The synthesis of the macromer, B, is suitably carried out at a temperature in the range of from about room temperature to approximately 80° C. Preferably, the temperature employed is not above 40° C. and most suitably within the range of about 30°–40° C. The conversion of the isocyano group is followed by infra-red spectroscopy or titration.

Another method for preparing the macromer is by reacting a hydroxyl-terminated prepolymer, e.g. polybutylene or polypropylene oxide, with acryloyl chloride, methacryloyl chloride or maleic anhydride and thus forming a macromer without connecting urethane linkages as, for example, a macromer of the formula $B_2$ or $B_1$, where Y is a direct bond.

The free radical copolymerization is started by an initiator capable of generating free peroxy or alkyl radicals in high enough concentration to initiate polymerization of the vinyl monomers employed at the synthesis temperature. Examples of suitable initiators are diisopropyl percarbonate, tert.-butyl peroctoate, benzoyl peroxide, decanoyl peroxide, lauroyl peroxide, succinic acid peroxide, methyl-ethyl-ketone peroxides, tert.-butyl-peroxy acetate and aziosobutyronitrile. If the polymerization is carried out in water, water-soluble peroxy compounds can be uxed, such as sodium, potassium or ammonium persulfate, as well as free radicals-generating redox systems, such as a persulfate-bisulfite combination. The initiator is suitably used in an amount of approximately 0.02–1 percent by weight of the reaction mixture. Other free radical generating mechanisms can be employed, such as γ-rays, electron-beams and UV-radiation.

The reaction is preferably carried out in an inert or anaerobic atmosphere if done in open molds. It is known that oxygen inhibits polymerization and gives rise to extended polymerization times for completion of the reaction. If closed molds are used to form the hydrogen article, the molds are composed of inert materials having low oxygen permeability and non-stick properties. Examples of suitable molding materials are Teflon ®, silicone rubber, polyethylene, and Mylar ®. Glass and metallic molds may be used if a suitable mold-releasing agent is employed.

Incorporation of the medicament into the hydrogel article may be accomplished either by dissolution or dispersion in the macromer solution, monomer solution or mixture thereof prior to addition of the free radical catalyst, or by diffusion of the medicament into the finished article after polymerization. If the medicament is inert to free radical attack it is preferred to dissolve or disperse it in the macromer solution, monomer solution or mixture thereof prior to polymerization. If the medicament is susceptible to free radical attack it is incorporated into the finished article, after polymerization, by diffusion from a solvent medium.

The hydrogel system, consisting essentially of the hydrophobic macromeric segment, B, and the hydrophilic segment $A_p$, may vary widely in composition and consequently the degrees of hydrophilicity and mechanical strength may be balanced to suit a wide variety of applications, such as for delivery systems for drugs, insecticides, herbicides, etc., as semi-permeable membranes in reverse osmosis, as body implants and bandages.

Hydrogels with leathery toughness in the dry state and high elongation in the wet state can be synthesized with water absorption ranging from low to high, dependent on the relative proportions of previously described components.

Hydrophilic membranes, which combine a relatively high wet strength with equilibrium water-contents of 5–50% are especially useful in applications, such as body-implants, bandages and semi-permeable membranes. For example, subcutaneous and intramuscular implants for the controlled release or medication must be capable of water absorption in a moderate range (15–25% by weight), yet be strong enough in the dry state and swollen state to withstand insertion and extraction procedures as well.

In addition to their suitability as medicament carriers, the hydrogels of the present invention are suitable for use as carriers for antiseptics, flavors, coloring agents, nutrients, insecticides, herbicides and the like. In particular, the hydrogels of the present invention may be swollen in an appropriate solvent containing the agent to be delivered; the solvent is evaporated, leaving the agent with the hydrogel particles. Upon contact with an aqueous environment, the agent will be released in a controlled manner.

Because of their wide range of water absorption characteristics and strength and elasticity, the hydrogels of the present invention are particularly suitable for use as intra-muscular and subcutaneous implants in warm-blooded animals. For the same reasons, the hydrogel materials of the present invention may be fashioned into substituted blood vessels or extracorporeal shunts without the necessary supporting matrix used with other relatively weak hydrogel materials.

The hydrogel materials of the present invention are also suitable for use as hydrophilic and non-thrombogenic coating, since they adhere strongly to glass, metal and plastic. Because of their high strength and elasticity, they make strong coatings with high abrasion resistance useful for the coating of boat hulls to discourage barnacle growth, or the coating of lenses and glass to prevent fogging in high humidity environments.

Another unique attribute of the hydrogels of the present invention is their flexibility in the dry state such that they take on the shape desired in the application. A further advantage of the hydrogels of the present invention is realized in the swollen state inasmuch as they do not become friable, but retain strenght and elasticity, even when fully equilibrated in an aqueous environment. These properties are particularly useful in membrane applications under pressure, such as in reverse osmosis apparatus for which the hydrogels of the present invention are suitable.

Hydrogels of the present invention with medicaments contained therein are also particularly suitable for use in the treatment of open wounds and burns, due to their flexible form-fitting nature and simultaneous capability to carry medicaments directly to the affected area. A particular advantage of the hydrogels in this application is their flexibility in the dry state. It is not necessary to pre-swell the hydrogel before application in order to make it soft and pliable enough to wrap large injured areas and, thus, the medicament-containing hydrogel may be stored dry, rather than swollen, thereby increasing the shelf life of the medication contained therein.

Any of the drugs used to treat the body, both topical and systemic, can be incorporated as the active agent in the copolymeric carrier of this invention. "Drug" is used herein in its broadest sense as including any composition of matter that will produce a pharmacological or biological response.

Suitable drugs for use in therapy according to this invention include, without limitations, those listed in U.S. Pat. No. 3,732,865 (columns 10 and 11).

Other drugs having the same or different physiological activity as those recited above can be employed in carriers within the scope of the present invention. Suitable mixtures of drugs can, of course, be dispensed with equal facility as with single component systems.

Drugs can be in various forms, such as uncharged molecules, components of molecular complexes, or non-irritating pharmacologically acceptable salts, e.g. the hydrochloride, hydrobromide, sulphate, phosphate, nitrate, borate, acetate, maleate, tartrate, salicylate, etc. For acidic drugs, salts of metals, amines, or organic cations (e.g. quaternary ammonium) can be employed. Furthermore, simple derivatives of the drugs (such as ethers, esters, amides, etc.) which have desirable retention and release characteristics but which are easily hydrolyzed by body pH, enzymes, etc., can be employed.

The amount of drug incorporated in the carrier varies widely depending on the particular drug, the desired therapeutic effect, and the time span for which it takes the drug to be released. Since a variety of carriers in a variety of sizes and shapes are intended to provide complete dosage regimes for therapy for a variety of maladies, there is no critical upper limit on the amount of drug incorporated in the carrier. The lower limit, too, will depend on the activity of the drug and the span of its release from the carrier. Thus, it is not practical to define a range for the therapeutically effective amount of drug to be released by the carrier.

Preferred drugs to be incorporated according to the present invention are those designed for long-term treatment so that multiple daily doses can be avoided, for example, anabolics, e.g. methandrostenolone; analgesics, e.g. acetylsalicylic acid, phenylbutazone or methadone; androgens, e.g. methyltestosterone; antibiotics, e.g. rifampin; antidepressants, e.g. imipramine or maprotiline; antidiabetics; e.g. phenformin; anticonvulsives, e.g. carbamazepine; antihistamines, e.g. tripelennamine; antihypertensives, e.g. hydralazine; antiinfectives, e.g. trimethoprim; antiparasitics, e.g. nifurtimox; antiparkinson agents, e.g. levodopa; antiphlogistics, e.g. naproxen; antitussives, e.g. benzonatate; appetite depressants, e.g. mazindol; bronchodilators, e.g. fenoterol; coronary dilators, e.g. fenalcomine; corticoids, e.g. dexamethasone; cytostatics, e.g. floxuridine; diuretics, e.g.

hydrochlorothiazide; hypnotics, e.g. glutethimide; neuroleptics, e.g. reserpine or thioridazine psycho-analeptics, e.g. glutethimide; neuroleptics, e.g. methylphenidate; tranquilizers, e.g. diazepam; uricosurics, e.g. sulfinpyrazone; vasodilators, e.g. isoproterenol.

In addition to drugs, there can be incorporated in the copolymers of the instant invention fragrances or food flavors, such as orange oil, citral, coffee, tea, lemon oil, synthetic lemon-lime flavor, strawberry flavor, vanilla, biacetyl, anise, lilac fragrance, pine fragrance, peppermint oil, oily orchids essence, anethole, ethylpropionate, ethyl acetate, acetaldehyde, menthol and spearmint, as well as pesticides including bactericides, fungicides, insecticides and nematocides, as well as herbicides.

Other examples for said biologically effective ingredients are listed in U.S. Pat. No. 3,660,563 (columns 3 to 7).

Because of the superior physical dry and wet state properties of the novel hydrogels, especially those containing polyurethanes as the macromer component, such hydrogels constitute a hybrid of a classical hydrgel and polyurethane and are especially useful as biomedical plastics having non-thrombogenic properties. Thus, they may be considered to be excellent candidates for synthetic skin in the treatment of burns, and artificial organs with regard to the construction thereof or as a coating material thereon. They can also be used as suture materials.

The hydrogel compositions may vary from 30-90% monomer (A) and 10-70% macromer (B), corresponding to typical degree of swelling of about 10-250%. The preferred compositions contain from about 15-50% macromer (B) and about 50-85% monomer (A), and range in their degree of swelling from 15-120%.

The following examples illustrate the preparation of (a) the macromers, (b) the hydrophilic copolymers and (c) the compositions of said copolymers with active ingredients selected from pharmaceutical, agricultural and cosmetic products.

If a resulting polymer has to be characterized, a 3 g protein is cut off, weighed and kept in a bottle with about 50 cc water at room temperature. After 96 hours the swollen sample is taken out, freed of excess surface water with tissue paper and reweighed to determine the degree of swelling which is $$DS = \frac{\text{weight of wet sample} - \text{weight of dry sample}}{\text{weight of dry sample}} \times 100$$

From the rest of the hydrogel sheet, 6 tensile bars are stamped out, 3 of which are allowed to swell in water to their equilibrium water content. Tensile strength and elongation of the dry and wet samples is determined with an Instron testing machine according to ASTM test method D-638, using a type IV testing bar.

The release rate of a durg, incorporated into the hydrogel, was determined by measuring continuously the characteristic UV absorption of a stirred volume of water containing hydrogel disc of 16 mm diameter and 0.8-1.0 mm thickness.

In the following examples the term "isocyanate terminated poly-tetramethylene oxide" refers to a poly-tetramethylene oxide chain terminated on both ends with 2,4-toluene diisocyanate. These compounds can be easily synthesized and are also commercially available under the brand name "ADIPRENE" from the DuPont de Nemours Chemical Comp., Wilmington, Del.

The first seven examples show the effect of varying amounts of the macromeric, hydrophobic crosslinking agents on the physical properties of polyhydroxyethylmethacrylate gels and their synthesis.

A: 2-hydroxyethylmethacrylate (HEMA)
B: isocyanate terminated polytetramethyleneoxide+-HEMA

EXAMPLE 1

An isocyanate terminated polytetramethyleneoxide of molecular weight 1500 (ADIPRENE 167) (20 g) was dissolved in 18 g of 2-hydroxyethylmethacrylate and allowed to react for 72 hours at room temperature. After 72 hours the disappearance of all isocyanate was verified by noting the lack of the characteristic infrared band due to isocyanate at 2270 $cm^{-1}$ in the infrared spectrum. This mixture was then admixed with diisopropyl percarbonate (0.08 g), injected into a mold having the form of a flat sheet with thickness of 1 mm, and placed in a circulating oven at 60° C. for 2 hours. The resulting rigid, transparent sheet was soaked in water for two days and dried under vacuum at 80° C. Equilibrium water content as well as tensile strength and elongation in the dry and wet state were measured.

EXAMPLE 2

The process of Example 1 was repeated with the exception that a isocyanate terminated polytetramethyleneoxide of molecular weight 3000 (ADIPRENE L-42) (2.0 g) was used. A tough, transparent sheet was obtained which was soaked in water for two days and dried under vacuum at 80° C. and tested as described in Example 1.

EXAMPLE 3

The process of Example 1 was repeated with 5.0 g of ADIPRENE 167 (molecular weight 1500) and 15.0 g of 2-hydroxyethylmethacrylate. The product was a tough, transparent sheet which was treated as described in Example 1.

EXAMPLE 4

The process of Example 1 was repeated except the composition was changed to 10.0 g of ADIPRENE 167 (molecular weight 1500) and 10.0 g of 2-hydroxyethylmethacrylate. A tough, transparent sheet was obtained which was treated as in Example 1.

EXAMPLE 5

The process of Example 2 was repeated except the composition was altered to 5.0 g of ADIPRENE L-42 (molecular weight 3000) and 15.0 g of 2-hydroxyethylmethacrylate. A tough, transparent sheet was obtained which was treated and tested as in Example 1.

EXAMPLE 6

The process of Example 2 was repeated using the composition of 10.0 g ADIPRENE L-42 (molecular weight 3000) and 10.0 g of 2-hydroxyethylmethacrylate. A tough, transparent sheet was obtained which was treated and tested as in Example 1.

EXAMPLE 7

As a control a conventional poly(2-hydroxyethyl)methacrylate gel was prepared using 1.2 percent ethylene glycol dimethacrylate as crosslinking agent and using otherwise the same procedure as for the previous gels. A hard, brittle, transparent sheet was obtained which was treated and tested as described. Table I shows a decreasing degree of swelling with increasing amounts of the hydrophobic macromer B. Dry state tensile strenght is higher, than for the conventional poly-HEMA of Ex. 7. Wet state tensile strength as well as elongation in the dry and wet state increase substantially with increasing amounts of B.

Table I

| Ex. No. | Macromer (B) % ADIPRENE* + HEMA | Monomer ($A_s$) HEMA % | DS | Tensile Str. (psi) Dry | Elongat. % Wet |
| --- | --- | --- | --- | --- | --- |
| 1 | L-167: 11.6 | 88.4 | 52 | 4560/41 | 185/99 |
| 2 | L-42: 10.8 | 89.2 | 42 | 5343/39 | 150/108 |
| 3 | L-167: 29 | 71 | 22 | 4760/89 | 409/113 |
| 4 | L-167: 58 | 42 | 12 | 4123/144 | 1055/150 |
| 5 | L-42: 27 | 73 | 30 | 4453/120 | 258/95 |
| 6 | L-42: 54 | 46 | 20 | 3167/246 | 557/214 |
| 7 | — | 98.5 | 45 | 2320/15 | 69/83 |

*ADIPRENE L-167: MW = 1500
ADIPRENE L-42: MW = 3000

The following examples show the usefulness of N-vinyl pyrrolidone as hydrophilic monomer (A) as well as the use of hydrophobic comonomers to adjust the equilibrium water content.

EXAMPLES 8–11

30 g of an isocyanate terminated polytetramethylene oxide of a molecular weight 3000 (ADIPRENE L-42) were dissolved in 40 g N-vinyl pyrrolidone and 10 g 2-hydroxyethyl methacrylate; after 72 hours all free isocyanate had disappeared. The solution was then divided into four equal parts and 5 g of the following monomers were added:
Ex. 8: N-vinyl pyrrolidone (NVP)
9: ethyl acrylate (EA)
10: dimethyl maleate (DMM)
11: vinyl acetate (VA)

To all four samples 0.1 g t-butyl-peroctoate were added and the solutions were poured into a sheet mold of 1 mm thickness. They were reacted at 80° C. for two hours, taken out of the mold and kept at 100° C. at 0.25 mm vacuum for 15 hours. The resulting sheets were clear and tough and their degree of swelling was determined:

Table II

| Ex. No. | Macromer (B) % ADIPRENE L-42 + HEMA | Monomer System (A) % + %($A_s$) NVP + HEMA | %($A_i$) Comonomer | D S |
| --- | --- | --- | --- | --- |
| 8 | 32.4 | 60 + 7.6 | — | 101 |
| 9 | 32.4 | 40 + 7.6 | EA: 20 | 75 |
| 10 | 32.4 | 40 + 7.6 | DMM: 20 | 78 |
| 11 | 32.4 | 40 + 7.6 | VA: 20 | 91 |
| 12 | 22.6 | 29 + 5.4 | EA: 43 | 42 |

In the following two examples the macromer (B) is a bisvinyl ether (Ex. 12) and a bis-maleate (Ex. 14).

EXAMPLE 13

Using the same procedure as described in Examples 8–11, 30 g isocyanate terminated polytetramethylene oxide (MW:3000) and 10 g 4-hydroxybutyl vinyl ether (HBVE), in 30 g N-vinyl pyrrolidone were reacted all free isocyanate had disappeared. Then 30 g ethyl acrylate were added to the mixture, and 0.4 g t-butyl-peroctoate. The mixture was poured into flat sheet molds and after 2 hours at 80° C. the crosslinked sheets were taken out of the mold. They were then kept for 16 hours in a vacuum over (0.25 mm Hg) at 100° C. The sample was a tough, clear sheet, whose degree of swelling was determined (see Table III).

EXAMPLE 14

Using the same procedure as described in Examples 8–11, 40 g isocyanate terminated polytetramethylene oxide (MW:3000), and 10 g 3-hydroxypropyl-butyl meleate (HPBM) in 50 g N-vinyl pyrrolidone were reacted until all free NCO had disappeared. 0.4 g t-butylperoctoate were added and the mixture poured into a flat sheet mold and cured at 80° C. for 2 hours. The crosslinked sheet was then taken out of the mold and kept for 16 hours in a vacuum oven (0.25 mm Hg) at 100° C. The sample was a tough, clear sheet whose degree of swelling was determined (see Table III).

Table III

| Ex. No. | Macromer (B) % ADIPRENE L-42 + | Capping Monomer | Monomer System (A) % $A_s$ NVP + HBVE HPBM | % $A_j$ Comonomers | D S |
| --- | --- | --- | --- | --- | --- |
| 13 | 32.4 | HBVE | 30 + 7.6 — | 30 | 72 |
| 14 | 43.1 | HPBM | 50 + — 6.9 | — | 89 |

In the following examples, the macromeric crosslinking agent contains linear polyesters and polypropylene oxide chains:

EXAMPLES 15–17

An isocyanate terminated polyester (Multrathane E-410, Mobay Chemical Corp.) of MW=425 was mixed with 2-hydroxyethyl methacrylate (HEMA) in the following proportions:
Ex. 15: 15 g polyester diisocyanate+85 g HEMA
16: 25 g polyester-diisocyanate+75 g HEMA
17: 40 g polyester-diisocyanate+60 g HEMA
The mixtures were allowed to stand at room temperature for 72 hours, after which time all isocyanate had reacted. Each sample was admixed with 0.4 g t-butyl proctoate and poured into a flat sheet mold of 1 mm thickness. The samples were cured at 80° C. for two hours, taken out of the mold and kept for 16 hours at 100° C. in a vacuum oven (0.25 mm Hg). The translucent sheets were tough and flexible, their degree of swelling is reported in table IV.

Table IV

| Ex. No. | % Macromer (B) Polyester (E-410) + HEMA | Monomer (A) % HEMA | D S |
|---|---|---|---|
| 15 | 23.4 | 76.6 | 30 |
| 16 | 39 | 61 | 21 |
| 17 | 62 | 38 | 21 |

EXAMPLES 18–19

A bis-maleimide type macromer (B), obtained by reaction of 2 moles maleic anhydride with 1 mole polypropylene oxide terminated with primary amino-groups and having a molecular weight of about 2200, (polypropylene oxide-bis-maleimide) was dissolved in 2-hydroxyethyl methacrylate in two different proportions:

Ex. 18: 20% polypropylene oxide/80% HEMA bis-maleimide

19: 35% polypropylene oxide/65% HEMA bismaleimide 0.1% t-butyl peroctoate was added and the solutions cured in flat-sheet molds at 80° C. for 2 hours; the sheets were taken out and kept at 100° C. for 16 hours in a vacuum oven (0.25 mm Hg); they were tough and flexible; their degree of swelling is reported in table V.

Table V

| Ex. No. | Macromer (B) % Polypropylene oxide bis-maleimide | Monomer (A) % HEMA | D S |
|---|---|---|---|
| 18 | 20 | 80 | 44 |
| 19 | 35 | 65 | 33 |

EXAMPLE 20

53.0 g polypropylene oxide - bismaleimide of Example 18 and 19 were dissolved in 47.0 g N-vinylpyrrolidone; 0.4 g tert-butylperoctoate were added and the mixture was filled in molds and cured as described in Example 18. The product was a tough, light brown gel, which absorbed 46.0% of its own weight of water (DS=46.0).

EXAMPLE 21

59.8 g polypropylene oxide-bismaleimide of Example 18 and 19 were dissolved in 27.1 g N-vinylpyrrolidone and 13.0 g ethylacrylate; 0.4 g tert-butylperoctoate were added and the mixture filled in molds and cured as described in Example 18. The gel was a tough, very light yellow sheet which absorbed 26.5% of its own weight of water (DS=26.5).

EXAMPLE 22

Example 21 was repeated, but the amounts of N-vinylpyrrolidone and ethylacrylate were 3.10 g and 26.4 g respectively. The product was tough, colorless gel which absorbed 23.0 % of its own weight of water (DS=23.0).

EXAMPLE 23

Example 21 was repeated, but the amounts of N-vinylpyrrolidone and ethylacrylate were 27.1 g and 43.5 g respectively. The product was a tough, colorless gel which absorbed 15.8% of its own weight of water (DS=15.8).

EXAMPLES 24–26

The process of Example 2 was repeated with the exceptions that the isocyanate terminated polytetramethyleneoxide of molecular weight 3000 (Adiprene L-42) was used in concentrations of 15% for Example 24, 25% for Example 25 and 33% for Example 26, and 2.0% (by weight) of Pyribenzamine HCl ®, a pharmaceutical with antihistamine properties, was dissolved in each specimen just prior to polymerization.

EXAMPLE 27

The process of Example 7 was repeated with the exception that 4% (by weight) of Pyribenzamine HCl was dissolved in the monomeric mixture just prior to polymerization.

Flat sheet specimens of equal thickness were taken from Examples 24–27 and extracted in HCl/NaCl solution (pH 2.15) at 37° C. for a period of 16 hours. The amount of the drug extracted from each sheet was measured at various times during the process by measuring the amplitude of the characteristic absorption peak of Pyribenzamine in the solution at 314 nm with a Beckman Acta C III ultraviolet spectrophotometer.

The time required to extract 50% of the Pyribenzamine was 2 hours, 4 hours and 6.5 hours for specimens taken from examples 24,25 and 26 respectively, illustrating the versatility in diffusion control of the present invention. By comparison, an equally thick specimen taken from the material of Example 27 delivered 50% of the dissolved drug in less than 1 hour.

EXAMPLES 28–29

The process of Example 1 was repeated with the exceptions that the isocyanate terminated polytetramethylene oxide is of molecular weight 600 (Adiprene L-315) and is used in concentrations of 20% by weight for Example 28 and 40% by weight for Example 29, and 3.7% of Dexamethasone, a synthetic steroid hormone, is dissolved in each specimen just prior to polymerization.

EXAMPLE 30

The process of Example 7 was repeated with the exception that 3.7% Dexamethasone was dissolved in the monomeric mixture just prior to polymerization.

Flat sheet specimens of approximately equal thickness were taken from Examples 28–30 and extracted in volumes of water at 25° C. for a period of 240 hours. The amount of the drug extracted from each sheet was measured at various times during the process by measuring the amplitude of the characteristic absorption peak of Dexamethasone in the solution at 242 nm with a Beckman Acta C III ultraviolet spectrophotometer.

It was found that more than 95% of the originally dissolved steroid was extracted from a specimen of the material from Example 30 within 140 hours, whereas, at the same time only 33% of the enclosed drug had been extracted from the material of Example 28 and only 12% of the steroid had been extracted from the material of Example 29, illustrating the utility of long term sustained release of water insoluble material from the present invention.

EXAMPLE 31

To 150 g N-vinyl pyrrolidone are added 200 g isocyanate terminated polytetramethylene oxide (MW 3000) and 50 g 2-hydroxyethyl methacrylate. The solution is stirred at 25° C. under an inert atmosphere for one week. At this time completion of the reaction between the diisocyanate and HEMA was confirmed by noting the disappearance of the NCO band in the infrared spectrum of the product. This product was stored and served as a masterbatch for the preparation of Examples 32–44.

EXAMPLE 32

Twenty grams of the masterbatch from Example 31 were mixed with (sufficient) t-butyl peroctoate catalyst (to bring the final catalyst concentration to 0.4% by weight). The mixture was charged into a closed mold in the form of a flat sheet approximately 1 mm in thickness. The mold was placed into a circulating air oven set at 80° C. for 2 hours to accomplish polymerization. The polymer sheet was then removed from the mold and subjected to a temperature of 80° C. at 0.1 mm pressure for 18 hours. The product was tough, clear sheet whose degree of swellig was determined.

EXAMPLE 33

The process of Example 32 was repeated with the exception that 1.0 g HEMA and 4 g N-vinyl pyrrolidone were added prior to addition of the peroxide.

EXAMPLE 34

The process of Example 32 was repeated with the exception that 2.0 g HEMA and 3.0 g N-VP were added prior to addition of the peroxide.

EXAMPLE 35

The process of Example 32 was repeated except that 4.0 g HEMA and 1.0 g N-VP were added to the masterbatch prior to adding the peroxide.

EXAMPLE 36

The process of Example 32 was repeated with the exception that 5.0 g HEMA were added prior to addition of the peroxide.

EXAMPLE 37

The process of Example 32 was repeated with the exception that 3.0 g N-VP and 27.0 g HEMA were added prior to addition of the peroxide.

EXAMPLE 38

The process of Example 32 was repeated with the exception that 24.0 g HEMA and 6.0 g N-VP were added prior to mixing in the peroxide.

EXAMPLE 39

The process of Example 32 was repeated except for the addition of 15.0 g each of N-VP and HEMA prior to addition of peroxide.

EXAMPLE 40

The process of Example 32 was repeated with the exception that 25.0 g HEMA and 5.0 g N-VP were mixed in prior to addition of the peroxide.

EXAMPLE 41

The process of Example 32 was followed with the exception that 3.53 g ethyl acrylate were added prior to peroxide addition.

EXAMPLE 42

The process of Example 32 was repeated except that 6.67 g ethyl acrylate were added prior to addition of the peroxide.

EXAMPLE 43

The process of Example 32 was repeated with the exception that 10.8 g ethyl acrylate were added prior to addition of the peroxide.

EXAMPLE 44

The process of Example 32 was followed except that 20.0 g ethyl acrylate were added prior to addition of the peroxide.

Compositions and degree of swelling for the gels of Examples 32–44 are tabulated in Table VII.

Table VII

| Ex. | Macromer (B), % Adiprene L-42 + HEMA | Monomer (A), % | | | Degree of Swelling |
|---|---|---|---|---|---|
| | | NVP | $A_s$ + | HEMA | $A_j$ EA | |
| 7 | — | — | | 98.5 | — | 52 |
| 32 | 54 | 37.5 | 8.5 | — | 26 | |
| 33 | 43.2 | 46 | 11.8 | — | 71 | |
| 34 | 43.2 | 42 | 14.8 | — | 60 | |
| 35 | 43.2 | 34 | 22.8 | — | 50 | |
| 36 | 43.2 | 30 | 26.8 | — | 41 | |
| 37 | 21.6 | 69 | 9.4 | — | 173 | |
| 38 | 21.6 | 63 | 15.4 | — | 153 | |
| 39 | 21.6 | 45 | 33.4 | — | 93 | |
| 40 | 21.6 | 25 | 53.4 | — | 55 | |
| 41 | 39.1 | 31.9 | 7.2 | 15 | 82 | |
| 42 | 34.5 | 28.1 | 6.4 | 25 | 71 | |
| 43 | 22.4 | 24.4 | 5.5 | 35 | 56 | |
| 44 | 23 | 18.8 | 4.2 | 50 | 28 | |

EXAMPLE 45

The polymer composition of Example 5 was cut into discs with 2.5 mm diameter and 1.0 mm thickness. 5.8 g of these discs were slurried in 50 ml of a 30% (by weight) solution of Pyribenzamine HCl in water for 48 hours at room temperature while stirring. The final weight of the swollen discs was 9.6 g. They were rinsed with distilled water and dried in vacuo (0.1 mmHg) at 60° C. to reach a constant weight, which was 6.85 g, corresponding to 15.3% of Pyribenzamine HCl within the polymer.

The sample released 50% of its total drug content in simulated gastric juice at 37° C. within 2 hours, and 85% within 9 hours.

EXAMPLE 46

A. Synthesis of Macromer Masterbatch:

2000 parts (1 mol) of poly-tetramethylene oxide of mol. weight 2000 (Polymeg 2000) are molten and poured into a 5 liter 3-neck flask and heated to 80° C. for one hour under vacuum to remove moisture. The vacuum is broken with dry nitrogen and the content cooled to 40° C. 444.6 parts (2 mol) isophorone diisocyanate are added, followed by 1 g triethylamine and the temperature is raised to 80°. After the NCO content has dropped to approximately 3.50 percent after 5 hours (determined by titration), the mixture is cooled to 40° C.

and 1630 parts HEMA (12.4 moles) are added, followed by 0.24 g dibutyltin dilaurate (DBTL). The mixture is left to cool to room temperature while being stirred under nitrogen until all NCO has disappeared (by IR).

B. Synthesis of Crosslinked, Hydrophilic Polymers:

The masterbatch prepared under A is used to make up monomer-macromer mixtures of the following compositions by adding either more HEMA or NVP:

| Example 46 | Composition | | |
|---|---|---|---|
| | Macromer (%) | HEMA (%) | NVP (%) |
| a | 68 | 32 | — |
| b | 45 | 55 | — |
| c | 34 | 66 | — |
| d | 11 | 89 | — |
| e | 22 | 53 | 25 |
| f | 22 | 33 | 45 |
| g | 22 | 15 | 63 |

To each monomer-macromer mixture 0.2 parts tert. butyl peroctoate are added and dissolved and the solutions are injected into glass molds (30×30 cm), lined with Mylar (polyester) sheets and using 1.6 mm silicone cord as spacer. Polymerization is carried out in a forced-air oven for 3 hours at 80° C. and 1 hour at 100° C. The molds are taken out, cooled to room-temperature and the sheets of hydrogel are taken out and characterized.

| Degree of Swelling, Tensile Strength (Wet and Dry) and Elongation (Wet and Dry) of HYdrogels a - g | | | | |
|---|---|---|---|---|
| Example No. 46 | D.S. % | Tensile Strength (psi) | | Elongation % | |
| | | Dry | Wet | Dry | Wet |
| a | 10 | 2720 | 1140 | 170 | 210 |
| b | 20 | 3460 | 490 | 130 | 160 |
| c | 27 | 4290 | 340 | 110 | 145 |
| d | 47 | 5910 | 120 | 50 | 120 |
| e | 61 | 5950 | 110 | 58 | 73 |
| f | 96 | 6620 | 85 | 67 | 60 |
| g | 138 | 7100 | 24 | 40 | 20 |

EXAMPLE 47

125.0 g (0.13 moles) of polyoxypropylene, MW 995, were poured into a 500 cc 3-neck reaction flask and dried at 80° C./2 mm Hg for 1 hour. The vacuum was broken with dry nitrogen gas and the content cooled to 40° C. 55.9 g (0.25 moles) isophorone diisocyanate and 127 mg triethylamine were added and the reaction temperature was raised to 80° C. After 18 hours the percent NCO was 5.80% (theoretical=5.84% NCO). The reaction mixture was cooled to 40° C. and 172.8 g (1.3 moles) of hydroxyethyl methacrylate were added to 115.2 g of reaction mixture. 9.6 mg of dibutyl tin dilaurate were added and the reaction mixture was kept at 40° C. until all NCO disappeared.

EXAMPLE 48

150.0 g (0.074 moles) of polyoxypropylene, MW 2015, were poured into a 500 cc 3-neck reaction flask and dried at 80° C./2 mm Hg for 1 hour. The vacuum was broken with dry nitrogen gas and the content cooled to 40° C. 33.1 g (0.15 moles) isophorone diisocyanate and 83 mg Dabco (1,4-diazabicyclo [2,2,2]octane, 1 mol %) were added and the reaction temperature was raised to 80° C. After 16 hours the percent NCO was 3.44% (theoretical=3.42% NCO). The reaction mixture was cooled to 40° C. and 179.3 g (1.4 moles) of hydroxyethyl methacrylate were added to 119.5 g of reaction mixture. 10 mg of dibutyl tin dilaurate were added and the reaction mixture was kept at 40° C. until all NCO disappeared.

EXAMPLE 49

143.9 g (0.050 moles) of polyoxypropylene, MW 2878, were poured into a 500 cc 3-neck reaction flask and dried at 80° C./2 mm Hg for 1 hour. The vacuum was broken with dry nitrogen gas and the content cooled to 40° C. 22.2 g (0.100 moles) isophorone diisocyanate and 56 mg Dabco (1 mole %) were added and the reaction temperature was raised to 80° C. After 12 hours the percent NCO was 2.44% (theoretical=2.53% NCO). The reaction mixture was cooled to 40° C. and 308.0 g (2.37 moles) of hydroxyethyl methacrylate were added to 205.3 g of reaction mixture. 17 mg of dibutyl tin dilaurate were added and the reaction mixture was kept at 40° C. intil all NCO disappeared.

EXAMPLE 50

145.9 g (0.074 moles) of molten polyester diol, MW 1965, were poured into a 500 cc 3-neck reaction flask and dried at 80° C./2 mm Hg for 1 hour. The vacuum was broken with dry nitrogen and the content cooled to 40° C. 33.0 g (0.15 moles) isophorone diisocyanate and 83 mg Dabco were added and the reaction temperature was raised to 80° C. After 7 hours the percent NCO was 3.48% (theoretical=3.49% NCO). The reaction mixture was cooled to 40° C. and 222.0 g (1.7 moles) of hydroxyethyl methacrylate were added to 148.0 g of reaction mixture. 12 mg of dibutyl tin dilaurate were added and the reaction was kept at 40° C. until all NCO disappeared.

EXAMPLE 51

To 50 g of the compositions prepared in Examples 47–50 0.1 g tert.-butyl peroctoate were added and dissolved under stirring. The mixture was degassed at room temperature at 1 mm Hg until no bubbles could be observed and poured into glass molds lined with Mylar polyester sheets and sealed with 1 mm silicone cord. The molds were heated in a circulating air oven to 80° C. for 3 hours, followed by 1 hour at 100° C. The sheets were stripped from the cooled molds and samples cut for analysis and physical testing.

| Degree of Swelling (DS) and Strength Data for Hydrogels Prepared in Examples 47-50 | | | | | |
|---|---|---|---|---|---|
| Example No. | D.S. % | Tensile Strength psi | | Elongation % | |
| | | Dry | Wet | Dry | Wet |
| 47 | 20 | 3980 | 433 | 89 | 111 |
| 48 | 22 | 3750 | 280 | 112 | 180 |
| 49 | 29 | 3600 | 250 | 113 | 126 |
| 50 | 19 | 4600 | 656 | 131 | 191 |

EXAMPLE 52

The composition of example 46d was polymerized into sheets the thickness of which ranged between 0.5 and 1.5 mm. The sheets were washed in running water at 40° C. for 3 days and various diameter tablets were cut from the sheets in the wet state. The tablets ranged from 4 mm to 1.2 mm in diameter after drying at 80° C. under vacuum.

EXAMPLE 53

The composition of example 46c was repeated and the resulting sheet was pulverized in a comminuting machine to produce multi-faceted particles of various average diameters. These particles were then washed in running water for 3 days at 40° C., dried and the particles classified according to particle size by passing them through a set of standard sieves with openings ranging from 2.4 to 0.18 mm. All material having praticle diameters smaller than 0.18 mm was discarded.

EXAMPLE 54

A tablet was selected from those produced in example 52 and was allowed to swell in a 40% aqueous solution of Tripelennamine HCl for a period of 48 hours, at which time it was rinsed with water and dried to constant weight. Weight gained by the tablet indicated that the final composition was 30.7% Tripelennamine HCl and the thickness of the specimen increased to 1.9 mm. The tablet, containing 37.2 mg Tripelennamine HCl, was placed into 1 liter of simulated gastric fluid at 37° C. and the amount of drug released was measured as a function of time spectrophotometrically. The release pattern was such that 25% of the total drug content was released at 0.5 hours, 50% at 2.2 hours, 75% at 5.5 hours and 90% at 10.5 hours.

EXAMPLE 55

The fraction of particles of example 53 having an average diameter of 1.4 mm was swollen in a 40% aqueous solution of Tripelennamine HCl for a period of 48 hours at which time it was rinsed with water and dried to constant weight. Weight gain by the particles indicated the final composition to be 17.5% Tripelennamine HCl. An amount of this fraction equivalent to 30 mg of the active ingredient was weighed into a fast dissolving capsule and placed into 1 liter of simulated gastric fluid at 37° C. The amount of Tripelennamine HCl released was measured as a function of time spectrophotometrically. The release pattern was such that 25% of the total drug content was released at 0.17 hours, 50% at 0.81 hours, 75% at 2.9 hours and 90% at 7.8 hours.

EXAMPLE 56

The fraction of particles of example 53 corresponding to an average diameter of 1.7 mm was swollen in a 22% solution of Phenformin HCl for a period of 48 hours. The solvent system used was a ethanol-water (3:1). After drying these particles had gained weight such that a total drug loading of 18% Phenformin HCl was indicated. An amount of this fraction equivalent to 50 mg of the active ingredient was weighed into a fast dissolving capsule and placed into 1 liter of simulated gastric fluid at 37° C. The amount of Phenformin HCl released was measured as a function of time spectrophotometrically. The release pattern was such that 25% of the total drug content was released at 0.75 hours, 50% at 2.25 hours, 75% at 5 hours and 90% at 9 hours.

EXAMPLE 57

A tablet from example 52 was selected and allowed to swell in a 30% aqueous solution of Imipramine HCl for 72 hours. After drying the tablet was found to be 0.75 mm thick and the increase in its weight indicated that it had a total drug loading of 33.6% Imipramine HCl. The tablet, containing 50 mg Imipramine HCl was placed into 1 liter of simulated gastric fluid at 37° C. and the amount of Imipramine HCl released was measured as a function of time spectrophotometrically. The release pattern was such that 25% of the total drug content was released at 1 hour, 50% at 2.5 hours, 75% at 5 hours and 90% at 8.75 hours.

EXAMPLE 58

The fraction of particles of example 53 having an average diameter of 0.425 mm was swollen in a 50% chloroform solution of Sulfinpyrazone for a period of 48 hours at which time it was rinsed with chloroform and dried to constant weight. The weight gained by the polymer indicated the final composition to be 10.3% Sulfinpyrazone. An amount of this fraction equivalent to 11.7 mg of the active ingredient was weighed into a fast dissolving capsule and placed into 1 liter of simulated gastric fluid at 37° C. The amount of Sulfinpyrazone released was measured as a function of time spectrophotometrically. The release pattern was such that 25% of the total drug content was released at 0.21 hours, 50% at 1.20 hours, 75% at 4.94 hours and 90% at 10.20 hours.

EXAMPLE 59

A tablet was selected from those produced in example 52 and was allowed to swell in a 21% aqueous solution of Hydralazine, which was produced by dissolving 10 g of Hydralazine HCl in 2 N-sodium hydroxide until the solution was complete and the pH of the solution was 8.0. Absorption into the tablet was allowed to proceed for 72 hours and upon drying the weight gained by the tablet indicated the final composition to be 10.7% Hydralazine. The tablet, containing 11 mg Hydralazine was placed into 1 liter of simulated gastric fluid at 37° C. and the amount of Hydralazine released was measured as a function of time spectrophotometrically. The release pattern was such that 25% of the total drug content was released at 0.53 nours, 50% at 3.33 hours, 75% at 7.87 hours and 90% at 13.3 hours.

EXAMPLE 60

The fraction of particles of example 53 having an average diameter of 1.4 mm was swollen in a 21% aqueous solution of Hydralazine which was produced by dissolving 10 g Hydralazine HCl in 2 N-sodium hydroxide until the solution was complete and the pH of the solution was 8.0. Absorption into the polymer was allowed to proceed for 72 hours and upon drying the weight gained by the polymer particles indicated the final composition to be 4.2% Hydralazine. The particles were filled into a fast dissolving capsule so as to produce a total dose of 20 mg. The capsule was placed into 1 liter of simulated gastric fluid and the release of Hydralazine was measured as a function of time spectrophotometrically. The release pattern was such that 25% of the total dose was released at 0.20 hours, 50% at 0.86 hours, 75% at 2.50 hours and 90% at 4.94 hours.

EXAMPLE 61

The fraction of particles of example 53 having an average diameter of 0.6 mm was swollen in a 22% solution of Maprotiline HCl which was produced by dissolving 10 g of Maprotiline HCl in 45 g of a methanol/chloroform solvent of composition 33 parts methanol and 67 parts chloroform. Absorption into the polymer was allowed to proceed for 48 hours and upon drying the weight gained by the polymer particles indicated the final composition to be 12.8% Maprotiline HCl. The particles were filled into a fast dissolving capsule so as to produce a total dose of 90 mg. The capsule was placed into 1 liter of simulated gastric fluid and the release of Maprotiline HCl was measured as a function of time spectrophotometrically. The release pattern was such that 25% of the total dose was released at 0.67 hours, 50% at 3.67 hours, 75% at 13.4 hours and 90% at 23.4 hours.

EXAMPLE 62

The fraction of particles of example 53 having an average diameter of 1.7 mm was swollen in a 26% solution of Methylphenidate HCl for a period of 48 hours at which time it was rinsed with water and dried overnight. The solvent system used was a mixture of methanol water (27:73). Weight gain by the particles indicated the final composition to be 26.7% Methylphenidate HCl. An amount of this solution equivalent to 270 mg of the active ingredient was weighed into a fast dissolving capsule and placed into 0.5 liter of simulated gastric fluid at 27° C. The amount of Methylphenidate HCl released was measured as a function of time spectrophotometrically. The release was such that 25% of the total dose was released at 0.67 hours, 50% at 3.0 hours, 75% at 7.8 hours and 90% at 14.2 hours.

EXAMPLE 63

15 g monomer-macromer mixture as described in Example 46c was blended with the following listed compounds as indicated below. 0.08 g tert.-butyl-peroctoate were mixed in, the solution or dispersion was degassed and injected into Mylar lined glass molds (30×30 cm) of 1.4 mm thickness, sealed by a silicone cord. The polymerization was carried out in a forced-air oven for 3 hours at 80° C. and 1 hour at 100° C. After the molds had cooled, the sample sheets were taken out and used for diffusion measurements.

| Example 63 | Active Ingredient Code | Grams | Appearance of Product |
|---|---|---|---|
| a | A | 15 | clear yellow flexible film |
| b | B | 15 | clear white flexible film |
| c | C | 15 | opaque yellow hard sheet |
| d | D | 15 | clear amber flexible film |
| e | E | 10 | clear white hard sheet |
| f | F | 3.8 | opaque off-white hard sheet |
| g | G | 3.8 | translucent yellow hard sheet |
| h | H | 5.0 | opaque white hard sheet |
| i | I | 15 | clear yellow hard sheet |

Explanation of Code:
A Ethyl 4,4′-dichlorobenzilate (miticide, acaricide)
B O-[5-Chloro-1-(1-methylethyl)-1H-1,2,4-triazol-3-yl] 0,0-diethyl phosphorothioate (insecticide)
C 2,6-dimethyl-N-β-methoxyethyl-chloracelanilide (herbicide)
D N′-(4-Chloro-o-tolyl)-N,N-dimethylformamidine (insecticide)
E 0,0-Dimethyl-phosphorodithioate S-ester with 4-(mercaptomethyl)-2-methoxyΔ$^2$-1,3,4-thiadiazolin-5-one (insecticide)
F 2-[4-Chloro-6-(cyclopropylamino)-1,3,5-triazin-2-yl-amino]-2-methylpropaneitrile (herbicide)
G S-[(6-chloro-2-oxooxazolo(4,5-b)pyridin-3(2H)-yl] ethyl)0,0-dimethyl phosphorothioate (insecticide)
H 2-(tert-Butylamino)-4-(ethylamino)-6-(methylthio)-s-triazine (herbicide)
I 0,0-diethyl-0-(2-isopropyl)-6-methyl-4-pyrimidinyl)phosphoro-thioate (in secticide) nematocide)

EXAMPLE 64

15 g monomer-macromer mixture as described in Example 46f were blended with the following listed compounds as indicated below. 0.08 g tert.-butyl peroctoate were mixed, the solution was degassed and injected into Mylar lined glass molds (30×30 cm) of 1.4 mm thickness, sealed by a silicone cord. The polymerization was carried out in a forced air oven for 3 hours at 80° C. and 1 hour at 100° C. After cooling the molds, the samples were taken out and used for diffusion measurements.

| Example 64 | Active Ingredient Code | Grams | Appearance of Product |
|---|---|---|---|
| a | K | 10 | opaque white hard sheet |
| b | L | 1.7 | clear yellow flexible sheet |
| c | M | 3.8 | white opaque hard sheet |

K disodium zinc ethylenediaminetetraacetate dihydrate (zinc supplement)
L 3-methyl-5-methylsulfonyl-1,2,4-thiadiazole (fungicide)
M 2-chloro-4,6-bis(ethylamino)-s-triazine (herbicide)

EXAMPLE 65

9.89 g of hydrophilic polymer prepared according to example 46b was immersed in 20 g N-(cyclopropylmethyl)-α,α,α-trifluoro-2,6-dinitro-N-propyl-p-toluidine (a herbicide) for 5 days. Then the polymer was removed, rinsed with methanol, air-dried and weighed. The dry polymer weighed 11.22 g corresponding to a polymer composition containing 11.8% active ingredient.

In a similar manner the polymer of example 46e was inbibed with sodium ferric ethylenediamine di-[o-hydroxyphenylacetate] (an iron supplement), 5% dissolved in methanol; the dried polymer contained 15% active ingredient.

EXAMPLE 66

Diffusion measurements were conducted at 25° C. in water buffered to a pH of 5 with secondary sodium citrate, by immersing a specimen of the delivery devices indicated in the table into 1 liter of stirred buffer solution. Aliquos were taken periodically and fractions of total active ingredients released from the polymers were determined spectrophotometrically.

| | Hours needed to obtain percent release | | | |
|---|---|---|---|---|
| Example 63 | 25% | 50% | 75% | 90% |
| a | 60 | | | |
| b | 3.0 | 7.5 | 18.0 | 30.0 |
| e | 4.2 | 16.5 | 50.0 | 170.0 |
| h | 9.0 | 35.0 | 120.0 | 300 |
| i | 12.0 | 48.0 | 72 | 72 |

EXAMPLE 67

The composition of example 63d was pulverized to a particle size of 0.18 to 0.25 mm, filled into a cylinder through which air was allowed to flow at a rate of 20 liters per minute at 40° C. The weight loss was followed gravimetrically and the fraction of active ingredient vaporized as calculated. The release rate was such that 25% was released after 48 hours, 50% at 300 hours, 75% after 1,050 hours and 90% at 2,000 hours.

EXAMPLE 68

Fragrances of known composition were incorporated into hydrogel polymer prepared according to the procedure described in Example 46c by polymerizing in the presence of 50% of the following mixtures:

|                       | Fragrances |      |        |         |        |          |
|-----------------------|------------|------|--------|---------|--------|----------|
| Formula               | Lilac      | Rose | Muguet | Jasmine | Violet | Carnation |
| Phenyl ethyl alcohol  | 30         | 35   | 15     | 5       | 20     | 25       |
| Hydroxy citronellal   | 30         | —    | 45     | 6       | 5      | 5        |
| Geraniol              | 2          | 48   | 20     | 2       | 4      | 5        |
| Amyl cinnamic aldehyde| 4          | 2    | 5      | 45      | 1      | 1        |
| Benzyl acetate        | 5          | 4    | 5      | 40      | 10     | 3        |
| Ionone                | 3          | 4    | 5      | —       | 60     | 4        |
| Eugenol               | 1          | 2    | —      | —       | —      | 55       |
| Terpineol             | 25         | 5    | 5      | 2       | —      | 2        |

All fragrances gave clear, transparent polymer-sheets which released the odors over a prolonged period of time.

EXAMPLE 69

Example 47 is repeated but instead of hydroxyethyl methacrylate an equal amount of 3-hydroxypropyl methacrylate is used to prepare the maromer-monomer mixture. It is polymerized as described in example 51. The resulting sheet is tough, flexible and transparent, and absorbs 15% water (D.S.=15).

EXAMPLE 70

The fraction of particles of example 53 having an average diameter of 0.6 mm was swollen in a 20% solution of Chlomipramine HCl which was produced by dissolving 10 g of Chlomipramine HCl in 40 g of water. Absorption into the polymer was allowed to proceed for 72 hours and upon drying the weight gained by the polymer particles indicated the final composition to be 10.6% Chlomipramine HCl. The particles were filled into a fast dissolving capsule so as to produce a total dose of 45 mg. The capsule was placed into 1 liter of simulated gastric fluid and the release of Chlomipramine HCl was measured as a function of time spectrophotometrically. The release pattern was such that 25% of the total dose was released at 0.5 hours, 50% at 2.2 hours, 75% at 5.9 hours and 90% at 11.0 hours.

EXAMPLE 71

The composition of example 46f was repeated with the exception that the thickness of the sheet produced was 1.15 mm. The sheet was washed in running water at 40° C. for 3 days and tablets having a diameter of 1.27 cm were cut after the sheet was thoroughly dried.

EXAMPLE 72

A tablet from example 71 was selected and allowed to swell in a 20% aqueous solution of Imipramine HCl for 48 hours. After drying the tablet was found to be 1.44 mm thick and the increase in its weight indicated that it had a total drug loading of 22.6% Imipramine HCl. The tablet, containing 46.3 mg Imipramine HCl was placed into 1 liter of simulated gastric fluid at 37° C. and the amount of Imipramine HCl released was measured as a function of time spectrophotometrically. The release pattern was such that 25% of the total drug content was released at 1.28 hours, 50% at 3.72 hours, 75% at 9.40 hours and 90% at 17.3 hours.

EXAMPLE 73

A tablet from example 71 was selected and allowed to swell in a 20% aqueous solution of Chlomipramine HCl for 48 hours. After drying, the tablet was found to be 1.38 cm thick and the increase in its weight indicated that it had a total drug loading of 19.5% Chlomipramine HCl. The tablet, containing 37.3 mg active ingredient was placed into 1 liter of simulated gastric fluid at 37° C. and the release of Chlomipramine HCl was measured as a function of time spectrophotometrically. The release pattern was such that 25% of the total dose was released at 1.33 hours, 50% at 4.03 hours, 75% at 10.2 hours and 90% at 18.7 hours.

We claim:

1. A controlled, sustained release composition comprising
   (a) a pharmaceutically, insecticidally or herbicidally effective agent in an amount at least sufficient for the total dosage during a treatment period, and
   (b) a water-insoluble hydrophilic gel comprising the crosslinked copolymerization product of
   (A) about 30 to about 90% by weight of said gel of (a) a water-soluble monoolefinic monomer, or mixture of said monomers, or (b) a water-soluble monomer, or mixture of said monomers with 1 to 50% by weight of total monomers of a water-insoluble monoolefinic monomer, or mixture of said water-insoluble monomers, with
   (B) about 10 to about 70% by weight of said gel of a terminal diolefinic hydrophobic macromer having a molecular weight from about 400 to about 8000, said macromer having the formula

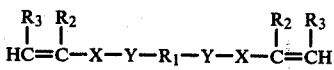

wherein $R_1$ is a polycondensate chain having a molecular weight from about 200 to about 8000, which is the residue of a poly(propylene oxide) or poly(tetramethylene oxide) glycol having ether linkages; $R_2$ is hydrogen, methyl or —$CH_2COOR_4$, wherein $R_4$ is hydrogen or an alkyl group with up to 10 carbon atoms; $R_3$ is hydrogen or $COOR_4$, with the proviso that at least one of $R_2$ and $R_3$ is hydrogen; X is oxa,—COO—, or —$CONR_5$—wherein $R_5$ is hydrogen or alkyl with up to 5 carbon atoms and Y is a direct bond or the radical —$R_6$—$Z_1$—CO—NH—$R_7$—NH—CO—$Z_2$—, wherein $R_6$ is linked to X and represents branched or linear alkylene with up to 7 carbon atoms; $Z_1$ and $Z_2$ is oxa or $NR_5$ and $R_7$ is the diradical of aliphatic or aromatic diisocyanate, with the proviso that in case X is oxa, Y is different from a direct bond, and $R_2$ and $R_3$ are hydrogen.

2. A composition as claimed in claim 1, wherein said water-soluble monomers are (a) acrylic or methacrylic acid, or water-soluble esters, amides or imides thereof, or (b) monoolefinic salts thereof or (c) polymers of a monoolefinic, monocyclic azacyclic monomer.

3. A composition as claimed in claim 1, wherein said water-soluble monomers are acrylic or methacrylic acid, hydroxyalkyl or dialkylaminoalkyl esters thereof, in which alkyl has 2 to 4 carbon atoms.

4. A composition as claimed in claim 1, wherein said water-soluble monomers are acrylic or methacrylic acid esters derived from the alcohol of the formula $$HO-C_mH_{2m}-O-(CH_2-CH_2-O)_n-R$$

wherein R is hydrogen or methyl, m is 2 to 5 and n is 1 to 20.

5. A composition as claimed in claim 1, wherein said water-soluble monomers are amides or imides of acrylic or methacrylic acid, in which the N-substituent is hydroxyalkyl, oxaalkyl or dialkylaminoalkyl, wherein alkyl has 2 to 4 carbon atoms.

6. A composition as claimed in claim 1, wherein said water-soluble monomers are acrylic acid, methacrylic acid, 2-hydroxyethyl or 2- or 3-hydroxypropyl acrylate or methacrylate, N-vinylpyrrolidone, or tert. aminomethacrylimide.

7. A composition as claimed in claim 1, wherein said water-soluble monomer is 2-hydroxyethyl methacrylate.

8. A composition as claimed in claim 1, wherein said water-soluble monomer is N-vinyl-2-pyrrolidone.

9. A composition as claimed in claim 1, wherein said water-soluble monomers are hydroxyalkyl maleates or fumarates, wherein alkyl has 2 to 4 carbon atoms.

10. A composition as claimed in claim 1, wherein said water-soluble monomers are hydroxyalkyl vinyl ethers, wherein alkyl has 2 to 4 carbon atoms.

11. A composition as claimed in claim 1, wherein said water-insoluble monomers are acrylonitrile or an alkyl acrylate or methacrylate, wherein alkyl has up to 18 carbon atoms.

12. A composition as claimed in claim 1, wherein said water-insoluble monomers are vinyl esters derived from an alkanecarboxylic acid having up to 5 carbon atoms.

13. A composition as claimed in claim 1, wherein said water-insoluble monomers are styrene or a vinyl alkyl ether, wherein alkyl has up to 5 carbon atoms.

14. A composition as claimed in claim 1, wherein $R_1$ is a polypropylene oxide or polytetramethylene oxide chain with a molecular weight of about 600 to about 4000.

15. A composition as claimed in claim 1, wherein said macromer is a polytetramethylene oxide glycol with a molecular weight of about 600 to about 4000, end-capped with toluene diisocyanate and reacted with 2 moles of a hydroxyakyl acrylate or methacrylate, wherein alkyl has 2 to 4 carbon atoms.

16. A composition as claimed in claim 1, wherein the polytetramethylene oxide glycol has a molecular weight of about 1500 to about 3000 and the hydroxyalkyl methacrylate is 2-hydroxyethyl methacrylate.

17. A composition as claimed in claim 1, wherein about 15 to about 50% of said macromer is used.

18. A composition according to claim 1 containing a pharmaceutically effective agent.

19. A composition according to claim 1 containing a insecticidally effective agent.

20. A composition according to claim 1 containing a herbicidally effective agent.

* * * * *